(12) United States Patent
Nasir et al.

(10) Patent No.: US 10,625,037 B2
(45) Date of Patent: Apr. 21, 2020

(54) INTUBATING AIRWAY DEVICE

(71) Applicants: Muhammed Aslam Nasir, Bedfordshire (GB); INTERSURGICAL AG, Vaduz (LI)

(72) Inventors: Muhammed Aslam Nasir, Bedfordshire (GB); Jane Elizabeth Kemp, Bristol (GB); Andrew Neil Miller, Crowthorne (GB)

(73) Assignees: INTERSURGICAL AG (LI); Muhammed Aslam Nasir (GB)

( * ) Notice: Subject to any disclaimer, the term of this patent is extended or adjusted under 35 U.S.C. 154(b) by 893 days.

(21) Appl. No.: 15/106,239

(22) PCT Filed: Dec. 17, 2014

(86) PCT No.: PCT/GB2014/053744
§ 371 (c)(1),
(2) Date: Jun. 17, 2016

(87) PCT Pub. No.: WO2015/092404
PCT Pub. Date: Jun. 25, 2015

(65) Prior Publication Data
US 2016/0331918 A1    Nov. 17, 2016

(30) Foreign Application Priority Data
Dec. 17, 2013    (GB) .................................. 1322328.4

(51) Int. Cl.
*A61M 16/04* (2006.01)
(52) U.S. Cl.
CPC .... *A61M 16/0445* (2014.02); *A61M 16/0409* (2014.02); *A61M 16/0438* (2014.02);
(Continued)

(58) Field of Classification Search
CPC ...... A61M 16/00; A61M 16/01; A61M 16/04; A61M 16/0409; A61M 16/0411;
(Continued)

(56) References Cited

U.S. PATENT DOCUMENTS

| 478,582 A | 7/1892 | Ermold .................... 128/207.14 |
| 2,099,127 A | 11/1937 | Leech ...................... 128/207.15 |

(Continued)

FOREIGN PATENT DOCUMENTS

| AU | B-52036/90 | 9/1990 | ............ A61M 16/04 |
| AU | B-45803/93 | 2/1994 | ............ A61M 16/04 |

(Continued)

OTHER PUBLICATIONS

Great Britain Combined Search and Examination Report issued in application No. GB1800914.2, dated Feb. 2, 2018 (6 pgs).
(Continued)

*Primary Examiner* — Rachel T Sippel
*Assistant Examiner* — Benjamin M. Kusiak
(74) *Attorney, Agent, or Firm* — Hayes Soloway P.C.

(57) ABSTRACT

An airway device for human or animal use includes an airway tube having a first end and a second end, the first end of which is surrounded by a laryngeal cuff configured to fit over the laryngeal inlet of a patient when in situ. The first end of the airway tube is provided with an intubating ramp configured to direct a tube inserted through the airway tube into the laryngeal inlet of the patient when in situ.

8 Claims, 4 Drawing Sheets

(52) U.S. Cl.
CPC .... *A61M 16/0463* (2013.01); *A61M 16/0488* (2013.01); *A61M 16/0497* (2013.01); *A61M 16/0415* (2014.02); *A61M 16/0436* (2014.02); *A61M 16/0443* (2014.02); *A61M 2250/00* (2013.01)

(58) Field of Classification Search
CPC .......... A61M 16/0415; A61M 16/0418; A61M 16/0434; A61M 16/0445; A61M 16/0447; A61M 16/045; A61M 16/0475; A61M 16/0477; A61M 16/0481; A61M 16/0484; A61M 16/0488; A61M 16/0497; A61M 2202/0007; A61M 2202/02; A61M 2202/0241; A61M 2202/0283; A61M 2202/0014; A61M 2205/16; A61M 2205/58; A61M 2210/0625; A61M 2210/065
USPC ............. 128/207.15, 207.14, 200.26, 204.18
See application file for complete search history.

(56) References Cited

U.S. PATENT DOCUMENTS

| | | | | |
|---|---|---|---|---|
| 3,443,564 | A | 5/1969 | Oehmig | 128/351 |
| 3,616,799 | A | 11/1971 | Sparks | 128/351 |
| 3,734,100 | A | 5/1973 | Walker et al. | 128/351 |
| 3,968,800 | A | 7/1976 | Vilasi | 128/343 |
| 3,995,643 | A | 12/1976 | Merav | 128/351 |
| 4,509,514 | A | 4/1985 | Brain | 128/207.15 |
| 4,846,791 | A | 7/1989 | Hattler | A61M 25/0026 |
| 4,913,139 | A | 4/1990 | Ballew | A61M 16/0488 |
| 4,919,126 | A | 4/1990 | Baildon | 128/207.14 |
| 4,987,895 | A * | 1/1991 | Heimlich | A61M 16/0465 128/207.14 |
| 4,995,388 | A | 2/1991 | Brain | 128/207.15 |
| 5,054,483 | A | 10/1991 | Marten et al. | 128/207.14 |
| 5,174,283 | A | 12/1992 | Parker | 128/200.26 |
| 5,181,505 | A | 1/1993 | Lew | 128/200.26 |
| 5,241,956 | A | 9/1993 | Brain | 128/207.15 |
| 5,249,571 | A | 10/1993 | Brain | 128/207.14 |
| 5,259,371 | A | 11/1993 | Tonrey | 128/200.26 |
| 5,282,464 | A | 2/1994 | Brain | 128/207.15 |
| 5,285,778 | A | 2/1994 | Mackin | 128/207.15 |
| 5,297,547 | A | 3/1994 | Brain | 128/207.15 |
| 5,303,697 | A | 4/1994 | Brain | 128/200.26 |
| 5,305,743 | A | 4/1994 | Brain | 128/207.15 |
| 5,309,906 | A | 5/1994 | LaBombard | 128/207.14 |
| 5,322,062 | A | 6/1994 | Servas | 128/207.14 |
| 5,339,805 | A | 8/1994 | Parker | 128/200.26 |
| 5,355,879 | A | 10/1994 | Brain | 128/207.15 |
| 5,391,248 | A | 2/1995 | Brain | 156/242 |
| 5,477,851 | A | 12/1995 | Callaghan et al. | 128/207.15 |
| 5,584,290 | A | 12/1996 | Brain | 128/207.15 |
| 5,605,149 | A | 2/1997 | Wafters | 128/207.14 |
| 5,618,267 | A | 4/1997 | Palestrant | 605/53 |
| 5,623,921 | A | 4/1997 | Kinsinger et al. | 128/200.26 |
| 5,632,271 | A * | 5/1997 | Brain | A61M 16/04 128/207.15 |
| 5,653,229 | A | 8/1997 | Greenberg | 128/207.15 |
| 5,655,519 | A | 8/1997 | Alfery | 128/200.26 |
| 5,682,880 | A | 11/1997 | Brain | 128/207.15 |
| 5,711,293 | A | 1/1998 | Brain | 128/200.24 |
| 5,791,341 | A | 8/1998 | Bullard | 128/207.15 |
| 5,827,243 | A | 10/1998 | Palestrant | A61M 25/0023 |
| 5,853,004 | A | 12/1998 | Goodman | 128/207.15 |
| 5,865,176 | A | 2/1999 | O'Neil | 128/207.15 |
| 5,878,745 | A * | 3/1999 | Brain | A61M 16/04 128/207.14 |
| 5,881,726 | A | 3/1999 | Neame | 128/207.15 |
| 5,896,858 | A * | 4/1999 | Brain | A61M 16/04 128/207.15 |
| 5,915,383 | A | 6/1999 | Pagan | 128/207.15 |
| 5,921,988 | A | 7/1999 | Legrand | 606/87 |
| 5,937,859 | A | 8/1999 | Augustine et al. | 128/207.15 |
| 5,937,860 | A | 8/1999 | Cook | 128/207.15 |
| 5,964,217 | A | 10/1999 | Christopher | 128/200.26 |
| 5,976,072 | A | 11/1999 | Greenberg | 600/120 |
| 5,979,445 | A | 11/1999 | Neame et al. | 128/207.15 |
| 5,988,167 | A * | 11/1999 | Kamen | A61M 16/04 128/207.14 |
| 6,003,514 | A | 12/1999 | Pagan | 128/207.15 |
| 6,055,984 | A | 5/2000 | Brain | 128/207.14 |
| 6,070,581 | A | 6/2000 | Augustine et al. | 128/207.15 |
| 6,079,409 | A | 6/2000 | Brain | 128/200.26 |
| D429,811 | S | 8/2000 | Bermudez | D24/110.5 |
| 6,095,144 | A | 8/2000 | Pagan | 128/207.15 |
| 6,152,136 | A | 11/2000 | Pagan | 128/207.15 |
| 6,216,696 | B1 | 4/2001 | van den Berg | 128/207.14 |
| 6,280,675 | B1 | 8/2001 | Legrand | 264/262 |
| 6,311,688 | B1 | 11/2001 | Augustine et al. | 128/200.26 |
| 6,318,367 | B1 | 11/2001 | Mongeon | 128/207.15 |
| 6,422,239 | B1 | 7/2002 | Cook | 128/207.15 |
| 6,439,232 | B1 | 8/2002 | Brain | 128/207.15 |
| 6,474,332 | B2 | 11/2002 | Arndt | 128/200.26 |
| 6,536,437 | B1 | 3/2003 | Dragisic | 128/207.18 |
| 6,604,525 | B2 | 8/2003 | Pagan | 128/207.15 |
| 6,631,720 | B1 | 10/2003 | Brain | 128/207.14 |
| D482,118 | S | 11/2003 | Dave et al. | D24/110 |
| 6,672,305 | B2 | 1/2004 | Parker | 128/200.26 |
| 6,679,263 | B2 | 1/2004 | Luchetti et al. | 128/207.15 |
| 6,698,430 | B2 | 3/2004 | Van Landuyt | 128/207.15 |
| 6,705,318 | B1 | 3/2004 | Brain | 128/207.14 |
| 6,705,321 | B2 | 3/2004 | Cook | 128/207.15 |
| 6,705,322 | B2 | 3/2004 | Chang | 128/207.15 |
| 6,792,948 | B2 | 9/2004 | Brain | 128/207.14 |
| 6,799,574 | B1 | 10/2004 | Collins | 128/207.15 |
| 6,827,710 | B1 | 12/2004 | Mooney | A61B 17/3417 |
| 6,877,512 | B2 | 4/2005 | Imai et al. | 128/207.15 |
| 6,918,388 | B2 | 7/2005 | Brain | 128/200.26 |
| 6,918,391 | B1 | 7/2005 | Moore | 128/842 |
| 6,971,382 | B1 | 12/2005 | Corso | 128/200.26 |
| 7,004,169 | B2 | 2/2006 | Brain | 128/207.14 |
| D518,572 | S | 4/2006 | Nasir | D24/110.5 |
| D518,890 | S | 4/2006 | Nasir | D24/110.5 |
| 7,040,312 | B2 | 5/2006 | Alfery et al. | 128/200.26 |
| 7,040,322 | B2 | 5/2006 | Fortuna | 128/207.15 |
| 7,047,973 | B2 | 5/2006 | Chang | 128/207.15 |
| 7,096,868 | B2 | 8/2006 | Tateo et al. | 128/207.15 |
| 7,097,802 | B2 | 8/2006 | Brain | 264/255 |
| 7,134,431 | B2 | 11/2006 | Brain | 128/200.26 |
| 7,140,368 | B1 | 11/2006 | Collins | 128/207.14 |
| D542,675 | S | 5/2007 | Luxton et al. | D9/749 |
| 7,263,998 | B2 * | 9/2007 | Miller | A61M 16/04 128/207.14 |
| RE39,938 | E | 12/2007 | Brain | 128/207.15 |
| 7,305,985 | B2 | 12/2007 | Brain | 128/200.26 |
| 7,357,845 | B2 | 4/2008 | Cook | 156/242 |
| 7,506,648 | B2 | 3/2009 | Brain | 128/207.15 |
| D611,138 | S | 3/2010 | Nasir | D24/110.5 |
| D615,188 | S | 5/2010 | Nasir | D24/110.5 |
| D618,788 | S | 6/2010 | Dubach | D24/110.5 |
| 7,762,261 | B1 * | 7/2010 | Fortuna | A61M 16/04 128/207.14 |
| 7,784,464 | B2 * | 8/2010 | Cook | A61M 16/0409 128/207.14 |
| 7,806,119 | B2 | 10/2010 | Nasir | 128/205.25 |
| 7,896,007 | B2 | 3/2011 | Brain | 128/207.15 |
| 7,900,632 | B2 * | 3/2011 | Cook | A61M 16/04 128/207.14 |
| 7,934,502 | B2 * | 5/2011 | Cook | A61M 16/04 128/200.26 |
| 8,001,964 | B2 | 8/2011 | McDonald et al. | 128/200.26 |
| D650,520 | S | 12/2011 | Timmermans | D27/163 |
| 8,091,242 | B2 | 1/2012 | Teys et al. | 30/324 |
| 8,215,307 | B2 | 7/2012 | Nasir | 128/207.15 |
| D665,495 | S | 8/2012 | Nasir | D24/110.5 |
| D668,759 | S | 10/2012 | Nasir | D24/110 |
| D693,920 | S | 11/2013 | Miller | D24/110.5 |
| D710,990 | S | 8/2014 | Brain | D24/110.5 |
| 8,809,682 | B2 | 8/2014 | Hepfinger | H02G 9/065 |
| D716,937 | S | 11/2014 | Brain | D24/110.5 |
| 9,265,905 | B2 | 2/2016 | Aslam | 128/207.15 |

(56) References Cited

U.S. PATENT DOCUMENTS

| | | | |
|---|---|---|---|
| D791,305 S | 7/2017 | Poulsen | D24/110.5 |
| D809,125 S | 1/2018 | Kheong | D24/110 |
| 2001/0015207 A1 | 8/2001 | Pagan | 128/207.15 |
| 2001/0025641 A1 | 10/2001 | Doane et al. | 128/207.15 |
| 2001/0027793 A1 | 10/2001 | Tielemans | 128/848 |
| 2002/0010417 A1 | 1/2002 | Bertram | 604/96.01 |
| 2002/0010617 A1 | 1/2002 | Hamaguchi et al. | 705/10 |
| 2002/0078961 A1 | 6/2002 | Collins | 128/207.15 |
| 2002/0103472 A1 | 8/2002 | Kramer | 604/507 |
| 2002/0108610 A1 | 8/2002 | Christopher | 128/200.26 |
| 2002/0112728 A1 | 8/2002 | Landuyt | 128/207.15 |
| 2002/0170556 A1 | 11/2002 | Gaitini | 128/200.14 |
| 2003/0037790 A1 | 2/2003 | Brain | 128/207.14 |
| 2003/0066532 A1 | 4/2003 | Gobel | 128/207.15 |
| 2003/0101998 A1 | 6/2003 | Zocca et al. | 128/207.15 |
| 2003/0136413 A1 | 7/2003 | Brain et al. | 128/207.15 |
| 2003/0172925 A1 | 9/2003 | Zocca et al. | 128/202.22 |
| 2003/0172933 A1 | 9/2003 | Nimmo | 128/207.14 |
| 2003/0213492 A1* | 11/2003 | Alfery | A61M 16/04 128/207.14 |
| 2004/0020488 A1 | 2/2004 | Kniewasser | 128/204.18 |
| 2004/0020491 A1 | 2/2004 | Fortuna | 128/207.15 |
| 2004/0060564 A1 | 4/2004 | Brain | A61M 16/00 |
| 2004/0200479 A1 | 10/2004 | Chang | 128/207.14 |
| 2005/0016529 A1 | 1/2005 | Cook | 128/200.24 |
| 2005/0051173 A1 | 3/2005 | Brain | 128/207.14 |
| 2005/0051175 A1 | 3/2005 | Brain | 128/207.14 |
| 2005/0066975 A1 | 3/2005 | Brain | 128/207.15 |
| 2005/0081861 A1 | 4/2005 | Nashir | 128/207.14 |
| 2005/0103345 A1 | 5/2005 | Brain | 128/207.15 |
| 2005/0104255 A1 | 5/2005 | Mejlhede et al. | 264/328.1 |
| 2005/0199244 A1 | 9/2005 | Tateo | A61M 16/04 |
| 2005/0274383 A1 | 12/2005 | Brain | 128/207.15 |
| 2006/0081245 A1 | 4/2006 | Gould | 128/200.26 |
| 2006/0207601 A1* | 9/2006 | Nasir | A61M 16/04 128/207.14 |
| 2007/0137651 A1 | 6/2007 | Glassenberg et al. | 128/207.15 |
| 2008/0099026 A1 | 5/2008 | Chang | 128/207.15 |
| 2008/0142017 A1 | 6/2008 | Brain | 128/207.15 |
| 2008/0236590 A1 | 10/2008 | Reissmann | 128/207.14 |
| 2008/0257356 A1 | 10/2008 | Swick | A61M 16/04 |
| 2008/0276932 A1* | 11/2008 | Bassoul | A61M 16/04 128/200.26 |
| 2008/0308109 A1* | 12/2008 | Brain | A61M 16/04 128/207.14 |
| 2009/0090356 A1* | 4/2009 | Cook | A61M 16/04 128/200.26 |
| 2009/0247868 A1 | 10/2009 | Chesnin | A61M 25/0032 |
| 2010/0059061 A1 | 3/2010 | Brain | 128/207.14 |
| 2010/0089393 A1 | 4/2010 | Brain | 128/203.12 |
| 2010/0126512 A1 | 5/2010 | Nasir | 128/207.14 |
| 2010/0147309 A1 | 6/2010 | Cuevas et al. | 128/207.14 |
| 2010/0242957 A1 | 9/2010 | Fortuna | 128/202.22 |
| 2010/0319704 A1 | 12/2010 | Nasir | 128/207.15 |
| 2011/0004197 A1 | 1/2011 | Sansoucy | A61M 25/0102 |
| 2011/0023890 A1 | 2/2011 | Baska | 128/207.15 |
| 2011/0120474 A1* | 5/2011 | Daugherty | A61M 16/04 128/207.17 |
| 2011/0226256 A1 | 9/2011 | Dubach | |
| 2011/0265799 A1 | 11/2011 | Lisogurski | 128/207.15 |
| 2011/0277772 A1 | 11/2011 | Nasir | 128/207.15 |
| 2012/0024292 A1 | 2/2012 | Sandmore et al. | 128/207.14 |
| 2013/0092172 A1 | 4/2013 | Nasir | 128/207.15 |
| 2013/0247917 A1 | 9/2013 | Brain | 128/207.15 |
| 2013/0269689 A1 | 10/2013 | Brain | A61M 16/04 |
| 2013/0324798 A1* | 12/2013 | Molnar | A61M 16/04 600/120 |
| 2014/0171855 A1 | 6/2014 | Mastri | A61M 39/1011 |
| 2015/0000672 A1 | 1/2015 | Jassell | 128/207.15 |
| 2015/0005743 A1 | 1/2015 | McCullough | A61M 25/1011 |
| 2015/0144134 A1 | 5/2015 | Dubach | A61M 16/0447 |
| 2015/0320962 A1 | 11/2015 | Bafile | A61M 16/0816 |
| 2016/0235934 A1 | 8/2016 | Poulsen | A61M 16/0409 |
| 2016/0317768 A1 | 11/2016 | Nasir et al. | A61M 16/0486 |
| 2016/0331918 A1 | 11/2016 | Nasir | A61M 16/0488 |
| 2017/0043111 A1 | 2/2017 | Hoftman | A61M 39/105 |
| 2017/0072154 A1 | 3/2017 | Hoftman | A61M 16/0816 |
| 2018/0221051 A1 | 8/2018 | Durkin | A61B 17/3423 |

FOREIGN PATENT DOCUMENTS

| | | | |
|---|---|---|---|
| AU | 200076743 | 5/2001 | A61M 16/04 |
| CA | 1 324 551 | 11/1993 | A61M 16/04 |
| CA | 2 191 749 | 12/1995 | A61M 16/40 |
| CA | 2 346 248 | 4/2000 | A61M 16/40 |
| CN | 1 351 509 | 5/2002 | A61M 16/04 |
| CN | 05251091 | 1/2016 | A61M 16/04 |
| DE | 43 30 032 | 4/1994 | H02N 2/00 |
| DE | 299 02 267 | 7/1999 | A61M 16/06 |
| DE | 102008052752 | 4/2010 | A61M 25/14 |
| EM | 000067210-0001 | 8/2003 | |
| EM | 000067210-0002 | 8/2003 | |
| EM | 000197124-0001 | 6/2004 | |
| EM | 000197124-0002 | 6/2004 | |
| EM | 000197124-0003 | 6/2004 | |
| EM | 000197124-0004 | 6/2004 | |
| EM | 000197124-0005 | 6/2004 | |
| EM | 000197124-0006 | 6/2004 | |
| EM | 000180757-0001 | 7/2004 | |
| EM | 000482195-0001 | 2/2006 | |
| EM | 000482195-0002 | 2/2006 | |
| EP | 0 277 797 | 8/1988 | A61M 16/04 |
| EP | 0 389 272 | 9/1990 | A61M 16/04 |
| EP | 0 448 878 | 10/1991 | A61M 16/04 |
| EP | 0 586 717 | 3/1994 | A61M 16/04 |
| EP | 0 794 807 | 9/1997 | A61M 16/00 |
| EP | 0 834 331 | 8/1998 | A61M 16/04 |
| EP | 0 857 492 | 8/1998 | A61M 16/04 |
| EP | 0 875 260 | 11/1998 | A61M 16/04 |
| EP | 0 884 061 | 12/1998 | A61M 16/04 |
| EP | 0 911 049 | 4/1999 | A61M 16/04 |
| EP | 0 935 971 | 8/1999 | A61M 16/04 |
| EP | 1 125 595 | 8/2001 | A61M 16/04 |
| EP | 1504870 | 2/2005 | |
| EP | 1 579 885 | 9/2005 | A61M 16/04 |
| EP | 1220701 | 3/2007 | A61M 16/04 |
| EP | 1169077 | 12/2007 | A61M 16/04 |
| EP | 1 875 937 | 1/2008 | A61M 16/04 |
| FR | 2 690 108 | 10/1993 | H02N 2/00 |
| FR | 2 807 307 | 10/2001 | A47J 37/06 |
| FR | 2 827 482 | 1/2003 | A24B 1/10 |
| FR | 2 851 107 | 8/2004 | H04R 11/06 |
| GB | 1 402 255 | 8/1975 | A61M 25/00 |
| GB | 2 113 348 | 8/1983 | B06B 1/16 |
| GB | 2 128 561 | 5/1984 | B60R 19/54 |
| GB | 2 168 256 | 6/1986 | A61M 16/04 |
| GB | 2 249 959 | 5/1992 | A61M 16/04 |
| GB | 2 267 034 | 11/1993 | A61M 25/02 |
| GB | 2 285 765 | 7/1995 | A61M 16/04 |
| GB | 2 317 342 | 3/1998 | A61M 16/04 |
| GB | 2 319 182 | 5/1998 | A61M 16/04 |
| GB | 2 323 292 | 9/1998 | A61M 16/04 |
| GB | 2 326 009 | 12/1998 | A61M 16/04 |
| GB | 2 330 312 | 4/1999 | A61M 16/04 |
| GB | 2 337 020 | 11/1999 | B29D 31/00 |
| GB | 2 359 996 | 9/2001 | A61M 16/04 |
| GB | 2 364 644 | 2/2002 | A61M 16/04 |
| GB | 2 373 188 | 9/2002 | A61M 16/04 |
| GB | 2 393 399 | 3/2004 | A61M 16/04 |
| GB | 2 404 863 | 2/2005 | A61M 16/04 |
| GB | 2 413 963 | 11/2005 | A61M 16/04 |
| GB | 2438799 | 12/2007 | A61M 16/04 |
| GB | 2 465 453 | 5/2010 | A61M 16/04 |
| GB | 2465453 A * | 5/2010 | A61D 7/04 |
| GB | 2479823 | 10/2011 | A61M 16/12 |
| GB | 2481538 | 12/2011 | A61M 16/04 |
| GB | 2481538 A * | 12/2011 | A61M 16/04 |
| GB | 2521375 | 6/2015 | A61M 16/04 |
| GB | 132546167 | 7/2017 | A61M 16/04 |
| IE | 922073 | 12/1993 | A61M 16/00 |
| JP | 6/277286 | 10/1994 | A61M 16/04 |
| JP | 2706567 | 1/1998 | A61B 1/00 |
| JP | 2007-509154 | 4/2007 | A61K 31/4409 |

(56) References Cited

FOREIGN PATENT DOCUMENTS

| TW | 224047 | 11/2004 | ............ B29C 45/76 |
|---|---|---|---|
| WO | WO91/12844 | 9/1991 | ............ A61M 16/04 |
| WO | WO 94/17848 | 8/1994 | ............ A61M 16/04 |
| WO | WO 97/12640 | 4/1997 | ............ A61M 16/00 |
| WO | WO 98/24498 | 6/1998 | ............ A61M 16/04 |
| WO | WO 98/50096 | 11/1998 | ............ A61M 16/00 |
| WO | WO 99/44665 | 9/1999 | ............ A61M 16/04 |
| WO | WO 00/09189 | 2/2000 | ............ A61M 16/04 |
| WO | WO 00/30706 | 6/2000 | ............ A61M 16/04 |
| WO | WO 00/61213 | 10/2000 | ............ A61M 16/04 |
| WO | WO 0112844 | 2/2001 | ............... C12Q 1/34 |
| WO | WO 01/13980 | 3/2001 | ............ A61M 16/04 |
| WO | WO 2011131974 | 10/2001 | ............ A61M 16/04 |
| WO | WO 0197890 | 12/2001 | ............ A61M 16/00 |
| WO | WO 02/32490 | 4/2002 | ............ A61M 16/04 |
| WO | WO 03/020340 | 3/2003 | ............ A61M 16/04 |
| WO | WO 03018094 | 3/2003 | ............ A61M 16/04 |
| WO | WO 2004/016308 | 2/2004 | ............ A61M 16/04 |
| WO | 02004/089453 | 10/2004 | |
| WO | WO 2005/016427 | 2/2005 | ............ A61M 16/04 |
| WO | WO2005027999 | 3/2005 | |
| WO | WO 2005/041864 | 5/2005 | ........... A61K 31/415 |
| WO | WO2005099800 | 10/2005 | ............ A61M 16/04 |
| WO | WO2006/125986 | 11/2006 | ............ A61M 16/04 |
| WO | WO 2009/129081 | 10/2009 | ............ A61M 16/04 |
| WO | WO 2009142821 | 11/2009 | ............... A61B 1/31 |
| WO | WO 2011161473 | 12/2011 | ............ A61M 16/04 |
| WO | WO 2014058840 | 4/2014 | ............ A61M 16/00 |
| WO | WO 2014159522 | 10/2014 | ............ A61M 16/04 |
| WO | WO2015092404 | 6/2015 | ............ A61M 16/04 |

OTHER PUBLICATIONS

Notice of Allowance issued in U.S. Appl. No. 14/375,109, dated Feb. 9, 2018 (8 pgs).
Office Action issued in U.S. Appl. No. 14/375,109, dated Dec. 15, 2017 (17 pgs).
Office Action issued in U.S. Appl. No. 29/548,655, dated Mar. 8, 2018, (7 pgs).
"The Development of the Laryngeal Mask—a Brief History of the Invention, Early Clinical Studies and Experimental Work from Which the Laryngeal Mask Evolved" A.I.J. Brain, European Journal of Anesthesiology, 1991, Supplement 4, pp. 5-17.
Combined Search and Examination Report issued in corresponding application No. GB1110775.2, dated Oct. 18, 2011 (8 pgs).
Combined Search and Examination Report issued in corresponding application No. GB0718849.3, dated Oct. 29, 2007 (4 pgs).
Combined Search and Examination Report issued in corresponding application No. GB0502519.2, dated Sep. 13, 2005 (6 pgs).
Combined Search and Examination Report issued in corresponding application No. GB1019839.8, dated Dec. 1, 2010 (2 pgs).
Combined Search and Examination Report issued in corresponding application No. GB 0418050.1, dated Nov. 29, 2004 (7 pgs).
Combined Search and Examination Report issued in related application No. GB1301478.2, dated May 23, 2013 (5 pgs).
Examination Report issued in corresponding application No. 09 756 353.0-1257, dated Aug. 17, 2012 (5 pgs).
Extended European Search Report and Written Opinion issued in corresponding EPO application No. 07019251.3, dated Feb. 1, 2008 (8 pgs).
First Office Action issued in corresponding Chinese application No. 200480023382.4, dated Aug. 22, 2008 (15 pgs).
Further examination as result of telephone conversation with examiner issued in corresponding EPO application No. 03 787 902.0 (1 pg).
Great Britain Combined Search and Examination Report issued in application No. GB1322330.0, dated May 20, 2015 (8 pgs).
Great Britain Combined Search and Examination Report issued in application No. GB1322328.4, dated Feb. 26, 2015 (8 pgs).
International Preliminary Report on Patentability issued in application No. PCT/GB2014/053744, dated Jun. 21, 2016 (9 pgs).
International Search Report and Written Opinion issued in Applicant's corresponding UK Patent Application Serial No. GB0817776.8, dated Jan. 8, 2009 (6 pgs).
International Search Report and Written Opinion issued in application No. PCT/GB2014/053745, dated Mar. 11, 2015 (14 pgs).
International Search Report and Written Opinion issued in application No. PCT/GB2014/053744, dated Jul. 14, 2015 (15 pgs).
International Search Report and Written Opinion issued in corresponding application No. PCT/GB2011/051203, dated Jul. 12, 2011 (14 pgs).
International Search Report and Written Opinion issued in corresponding application No. PCT/GB2011/051203, dated Dec. 7, 2011 (15 pgs).
International Search Report and Written Opinion issued in corresponding PCT application No. PCT/GB2009/051574, dated Jun. 7, 2010 (28 pgs).
International Search Report and Written Opinion issued in related application No. PCT/GB2013/050180, dated May 7, 2013 (13 pgs).
International Search Report issued in corresponding PCT application PCT/GB03/03577 dated Aug. 14, 2003 (9 pgs).
Invitation to Pay Additional Fees with International Search Report issued in corresponding application No. PCT/GB2004/003481, dated Nov. 12, 2004 (8 pgs).
Notice for Reasons for Rejection issued in corresponding Japanese application No. 2006/523053, dated Nov. 8, 2010, with English translation (4 pgs).
Notice of Allowance issued in U.S. Appl. No. 13/805,956, dated Dec. 21, 2015 (26 pgs).
Notice of Allowance issued in U.S. Appl. No. 14/315,141, dated Nov. 13, 2015 (36 pgs).
Notice of Allowance issued in U.S. Appl. No. 14/315,149, dated Mar. 11, 2016 (42 pgs).
Notice of Allowance issued in U.S. Appl. No. 29/428,284, dated Mar. 8, 2016 (17 pgs).
Notice of Allowance issued in related U.S. Appl. No. 13/403,806, dated Mar. 12, 2014 (16 pgs).
Notice of Allowance issued in related U.S. Appl. No. 29/416,561, dated May 9, 2014 (7 pgs).
Notice of Allowance issued in related U.S. Appl. No. 29/449,900, dated Jul. 24, 2013 (11 pgs).
Notice of Allowance issued in related U.S. Appl. No. 29/407,461, dated Jun. 12, 2013 (26 pgs).
Office Action issued in U.S. Appl. No. 12/627,844, dated May 5, 2016 (33 pgs).
Office Action issued in U.S. Appl. No. 12/627,844, dated Sep. 17, 2015 (26 pgs).
Office Action issued in U.S. Appl. No. 29/353,658 dated Aug. 19, 2011 (10 pgs).
Office Action issued in U.S. Appl. No. 29/428,284, dated Mar. 19, 2015 (6 pgs).
Office Action issued in U.S. Appl. No. 29/428,284, dated Nov. 10, 2015 (5 pgs).
Office Action issued in U.S. Appl. No. 29/512,931, dated Mar. 8, 2016 (8 pgs).
Office Action issued in U.S. Appl. No. 29/51.2,931, dated Nov. 23, 2015 (20 pgs).
Office Action issued in U.S. Appl. No. 29/512,932, dated Mar. 8, 2016 (8 pgs).
Office Action issued in U.S. Appl. No. 29/512,932, dated Nov. 19, 2015 (19 pgs).
Office Action issued in related U.S. Appl. No. 12/627,844, dated Feb. 28, 2014 (22 pgs).
Office Action issued in related U.S. Appl. No. 12/627,844, dated Oct. 23, 2014 (38 pgs).
Office Action issued in related U.S. Appl. No. 13/130,555, dated Jun. 20, 2014 (36 pgs).
Office Action issued in related U.S. Appl. No. 13/403,806, dated Apr. 25, 2013 (6 pgs).
Office Action issued in related U.S. Appl. No. 13/403,806, dated Aug. 15, 2013 (45 pgs).
Office Action issued in related U.S. Appl. No. 29/428,284, dated Oct. 6, 2014 (66 pgs).

(56) References Cited

OTHER PUBLICATIONS

Office Action issued in related U.S. Appl. No. 29/475,489, dated Jun. 20, 2014 (25 pgs).
Office Action issued in related U.S. Appl. No. 29/475,489, dated Dec. 4, 2014 (13 pgs).
PCT International Search Report, PCT Application Serial No. PCT/GB2008/050880, dated Jan. 14, 2009 (20 pgs).
U.S. Official Action dated Feb. 14, 2013, issued in U.S. Appl. No. 29/407,461 (21 pgs).
U.S. Appl. No. 12/627,844, filed Nov. 30, 2009, Nasir.
U.S. Appl. No. 14/375,109, filed Jul. 28, 2014, Jassell et al.
U.S. Appl. No. 29/548,655, filed Dec. 15, 2015, Miller et al.
Office Action issued in U.S. Appl. No. 14/375,109, dated Nov. 7, 2016 (17 pgs).
Office Action issued in U.S. Appl. No. 12/627,844, dated Jan. 27, 2017 (28 pgs).
Great Britain Combined Search and Examination Report Issued in Corresponding Application No. GB1621321.7, dated May 4, 2017 (5 Pages).
Great Britain Examination Report Issued in Corresponding Application No. GB1322330.0, dated Mar. 8, 2016 (3 Pages).
European Patent Office Examination Report Issued in Corresponding Application No. 14824070.8, dated Apr. 24, 2017 (9 Pages).
Official Action issued in U.S. Appl. No. 14/375,109, dated Jun. 23, 2017 (10 pgs).
U.S. Appl. No. 29/428,284, filed Jul. 27, 2012, Nasir et al.
U.S. Appl. No. 14/315,149, filed Jun. 25, 2014, Nasir.
U.S. Appl. No. 29/512,931, filed Dec. 23, 2014, Nasir et al.
U.S. Appl. No. 29/512,932, filed Dec. 23, 2014, Nasir et al.
Office Action issued in U.S. Appl. No. 14/375,109, dated Aug. 10, 2016 (49 pgs).
Notice of Allowance issued in U.S. Appl. No. 14/315,149, dated Aug. 30, 2016 (16 pgs).
Notice of Allowance issued in U.S. Appl. No. 29/548,655, dated Oct. 11, 2018 (28 pgs).
Great Britain Search and Examination Report issued in application No. GBP7665X, dated May 31, 2019 (7 pgs).
Great Britain Search and Examination Report issued in application No. GBP7665, dated May 1, 2019 (9 pgs).
Merriam-Webster Lumen Definition (Year: 2019) (1 pg).
Office Action issued in U.S. Appl. No. 15/106,243, dated Aug. 2, 2019 (18 pgs).
Action issued in U.S. Appl. No. 29/676,952, dated Jun. 6, 2019 (22 pgs).
U.S. Appl. No. 10/983,199, filed Nov. 5, 2004.
U.S. Appl. No. 10/568,362, filed Feb. 14, 2006.
U.S. Appl. No. 12/627,844, filed Nov. 30, 2009.
U.S. Appl. No. 29/353,658, filed Jan. 12, 2010.
U.S. Appl. No. 12/680,731, filed Mar. 29, 2010.
U.S. Appl. No. 12/859,169, filed Aug. 18, 2010.
U.S. Appl. No. 13/130,555, filed May 20, 2011.
U.S. Appl. No. 29/402,009, filed Sep. 19, 2011.
U.S. Appl. No. 29/407,461, filed Nov. 29, 2011.
U.S. Appl. No. 13/403,806, filed Feb. 23, 2012.
U.S. Appl. No. 29/416,561, filed Mar. 23, 2012.
U.S. Appl. No. 29/428,284, filed Jul. 27, 2012.
U.S. Appl. No. 13/805,956, filed Dec. 20, 2012.
U.S. Appl. No. 29/449,900, filed Mar. 15, 2013.
U.S. Appl. No. 29/475,489, filed Dec. 3, 2013.
U.S. Appl. No. 14/315,141, filed Jun. 25, 2014.
U.S. Appl. No. 14/315,149, filed Jun. 25, 2014.
U.S. Appl. No. 14/375,109, filed Jul. 28, 2014.
U.S. Appl. No. 29/512,931, filed Dec. 23, 2014.
U.S. Appl. No. 29/512,932, filed Dec. 23, 2014.
U.S. Appl. No. 29/548,655, filed Dec. 15, 2015.
U.S. Appl. No. 15/106,243, filed Jun. 17, 2016.
U.S. Appl. No. 29/676,952, filed Jan. 16, 2019.
U.S. Appl. No. 29/698,547, filed Jul. 17, 2019.
U.S. Appl. No. 15/106,243, filed Jun. 17, 2016, Nasir et al.
U.S. Appl. No. 29/676,952, filed Jan. 16, 2019, Miller et al.
U.S. Appl. No. 29/698,547, filed Jul. 17, 2019, Nasir et al.
Notice of Allowance issued in U.S. Appl. No. 29/676,952, dated Nov. 5, 2019 (5 pgs).
Office Action issued in U.S. Appl. No. 15/106,243, dated Jan. 10, 2020 (23 pgs).

* cited by examiner

INTUBATING AIRWAY DEVICE

FIELD OF THE INVENTION

The present invention relates to medical devices and is applicable to laryngeal airway devices and to their methods of manufacture. It is particularly applicable to devices used in the administration of Oxygen and/or anaesthetic gases to a human or veterinary patient breathing spontaneously, for Intermittent Positive Pressure Ventilation (IPPV) during a surgical procedure or resuscitation and for intubating patients during such procedures.

BACKGROUND TO THE INVENTION

GB2393399 (Nasir) describes an airway device comprising an airway tube having a first end and a second end, the first end of which is surrounded by a non-inflatable laryngeal cuff which forms an anatomical fit over the laryngeal inlet of a patient and a buccal cavity stabiliser located on or around the airway tube between the laryngeal cuff and the second end of the tube, the buccal stabiliser being adapted to prevent rotational or side-to-side movement of the airway device in use.

Whilst such airway devices provide a significant improvement over the use of inflatable cuff airway devices, it is still sometimes necessary to intubate a patient during a procedure.

A number of attempts have been made to provide for an airway device which not only forms an external seal around the laryngeal inlet of the patient, but also serves as a guide to allow for the insertion of an endotracheal tube. However, such devices have always been inflatable, do not always provide for the endotracheal tube to be guided directly into the laryngeal inlet and instead can direct the endotracheal tube into the oesophagus of the patient, and can cause the airway tube of the airway device to become blocked cutting off the air supply to the patient.

SUMMARY OF THE INVENTION

A first aspect of the present invention provides an airway device as described in the accompanying claims.

Accordingly, according to a first aspect of the present invention, there is provided an airway device for human or animal use comprising an airway tube having a first end and a second end, the first end of which is surrounded by a laryngeal cuff configured to fit over the laryngeal inlet of a patient when in situ, wherein the first end of the airway tube is provided with an intubating ramp configured to direct a tube inserted through the airway tube into the laryngeal inlet of the patient when in situ. Preferably the tube is an endotracheal tube.

In prior art devices such as that described in GB2393399 (Nasir), and as illustrated in FIG. 1, when an endotracheal tube is inserted through the airway tube, the endotracheal tube, instead of following its natural curve (which allows for correct insertion of the endotracheal tube into the laryngeal inlet), follows the curvature of the airway tube of the airway device. This often leads to the endotracheal tube, instead of entering the laryngeal inlet, sliding along the inside of the laryngeal cuff towards the tip of the device which can result in contact between the endotracheal tube and the larynx of the patient, and even insertion of the endotracheal tube into the oesophagus of the patient, both of which are undesirable.

However, in the present invention the airway device is provided with an intubating ramp which ensures that the endotracheal tube, when inserted through the airway tube, follows its natural curve, rather than the curve of the airway tube, and guides the endotracheal tube into the laryngeal inlet of the patient when the airway device is in situ in a patient.

Preferably the intubating ramp is provided on the internal wall of the dorsal side of the airway tube. In the alternative the intubating ramp is provided on the internal surface of the dorsal side of the laryngeal cuff. Preferably the ramp is angled to ensure that when the tube is inserted through the airway tube when the device is in situ in a patient, it exists the device higher up in the anatomy of the patient and is guided into the laryngeal inlet of the patient.

Preferably in addition to the intubation ramp, the first end of the airway tube is of greater diameter and thus wider than the remainder of the airway tube. In particular it is preferred that the internal surface of the ventral side of the airway tube is flattened rather than curved to provide this widening. This further enables the endotracheal tube, when inserted through the airway tube, to follow its natural curve, rather than the curve of the airway tube, and works in combination with the intubating ramp. Essentially what is created by the widening is a flaring at the first end of the airway tube as the airway tube emerges into the rear of the cuff.

Preferably the intubating ramp is provided with a channel or groove. Preferably the channel or groove runs longitudinally along the full length of the intubating ramp from the first end to the second end of the longitudinal ramp. More preferably the intubating ramp is provided with a plurality of channels or grooves. The provision of the intubating ramp reduces the depth of the internal cavity of the laryngeal cuff, this means that should the device be sub-optimally inserted that there is risk that the airway of the patient could become partially occluded. The provision of the one or more channel(s) or groove(s) ensures the patency of the airflow through the airway device into the airway of the patient without compromising the effect of the ramp.

Preferably the tip of the laryngeal cuff is elongate. Preferably the tip of the laryngeal cuff is provided with a protrusion or bump on the back dorsal side thereof. The elongate nature of the tip of the laryngeal cuff along with the dorsal protrusion or bump both assist to provide an improved oesophageal seal when the airway device is in situ in the patient. By providing an improved oesophageal seal there is reduced risk of inflation of the stomach of the patient, and a reduced risk of regurgitation entering into the airway of the patient.

Preferably a side wall of the second end of the airway tube is provided with a supplementary gas inlet. The supplementary gas inlet allows for additional oxygen or other gas to be provided to the patient if required. A suitable supplementary gas inlet has been described in WO2011131974 (Miller).

Preferably the cuff is non-inflatable and is pre-formed in a shape adapted to form an anatomical fit over the laryngeal framework of a patient.

Preferably the laryngeal cuff is pre-formed, pre-inflated with air or pre-filled with a suitable fluid. Most preferably the laryngeal cuff is non-inflatable, however in the alternative the laryngeal cuff can be inflatable.

In one alternative the airway device further comprises a buccal cavity stabiliser located on or around the airway tube between the laryngeal cuff and the second end of the tube. The buccal cavity stabiliser, if provided, may be formed from the same material as the cuff or from a different material and assists in locating and maintaining the position of the device in use.

In a particularly preferred embodiment the buccal cavity stabiliser, if provided, is formed as an integral part of the airway tube, and further preferably the buccal cavity stabiliser, the airway tube and the laryngeal cuff are all formed as an integral unit.

In a further alternative no buccal cavity stabiliser is provided.

The Shore hardness of the various, parts, portions or components is an important feature of the invention. For example, the laryngeal cuff is preferably formed from a material with a Shore hardness on the A scale of 40 or less and more preferably 000 to 20, and most preferably 000 to 4.

Preferably the laryngeal cuff and a front, ventral part of the buccal cavity stabiliser, if provided, are formed from a material of substantially the same Shore hardness. This simplifies construction and ensures that all portions of the device that come into firm contact with the patient's soft tissue are relatively soft.

In a further preferred embodiment a back or dorsal part of the device and a front or ventral part of the device are formed from materials of different Shore hardness. This enables the dorsal portion to be made of a firmer material than the ventral portion.

Preferably the back or dorsal part of the device is formed from a material of Shore hardness less than 60 on the A scale, more preferably 25 to 45, and most preferably 30 to 40.

Preferably the device further incorporates a gastric tube passageway extending from the tip of the cuff to the second end of the airway device.

According to a second aspect of the invention there is provided an airway device for human or animal use comprising an airway tube having a first end and a second end, the first end of which is surrounded by a laryngeal cuff configured to fit over the laryngeal inlet of a patient when in situ, wherein the first end of the airway tube is of widened diameter or flared.

BRIEF DESCRIPTION OF THE DRAWINGS

The invention will now be described, by way of example only, with reference to the accompanying drawings in which.

DESCRIPTION OF THE PREFERRED EMBODIMENTS

Figure 1:
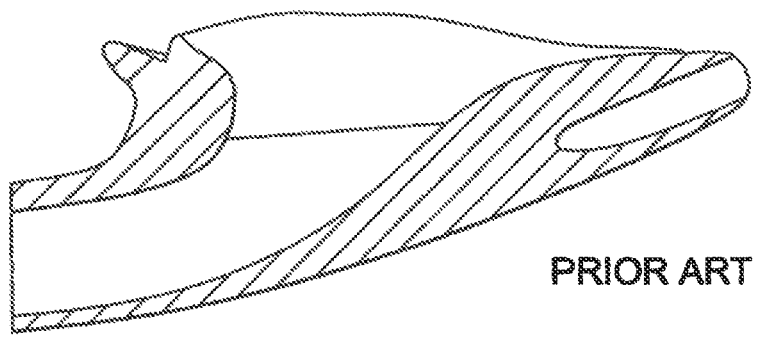
FIG. 1 illustrates a part cross-sectional view of the laryngeal cuff of the prior art.
Figure 2:
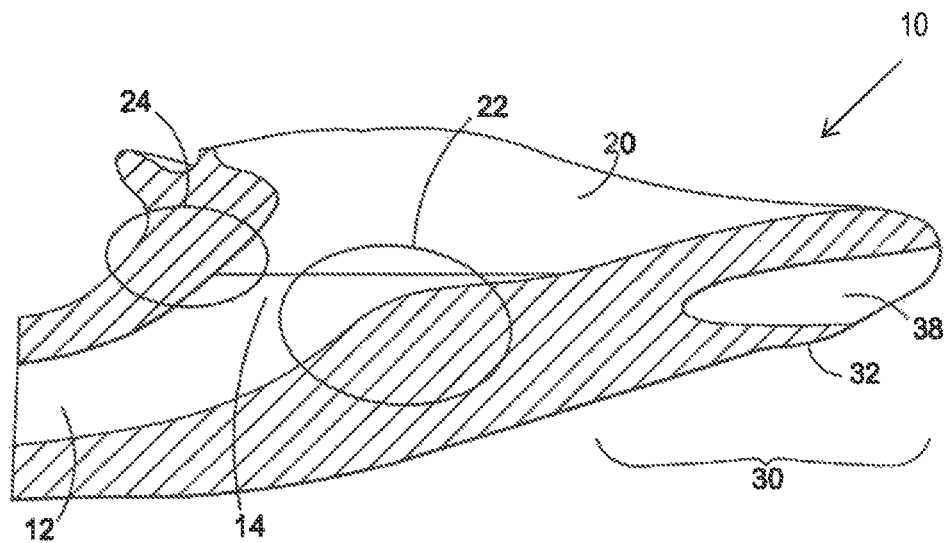
FIG. 2 illustrates a part cross-sectional view of the laryngeal cuff according to a first embodiment.
Figure 3:
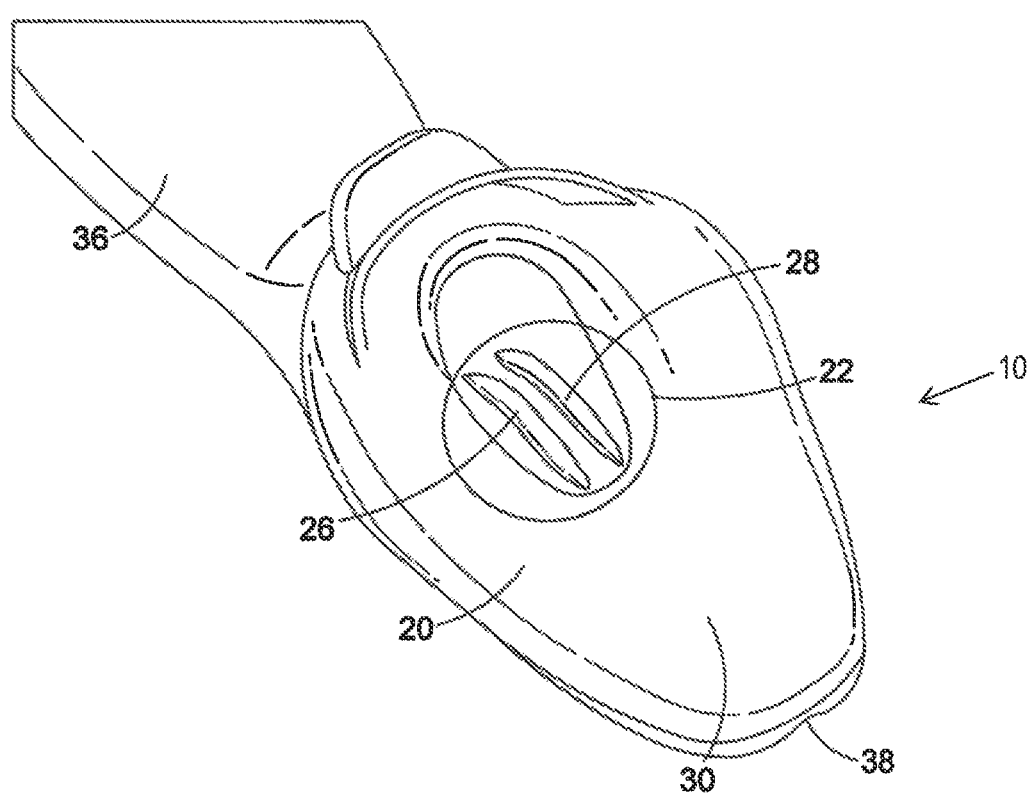
FIG. 3 illustrates a front ventral perspective view of the laryngeal cuff according to a first embodiment.
Figure 4:
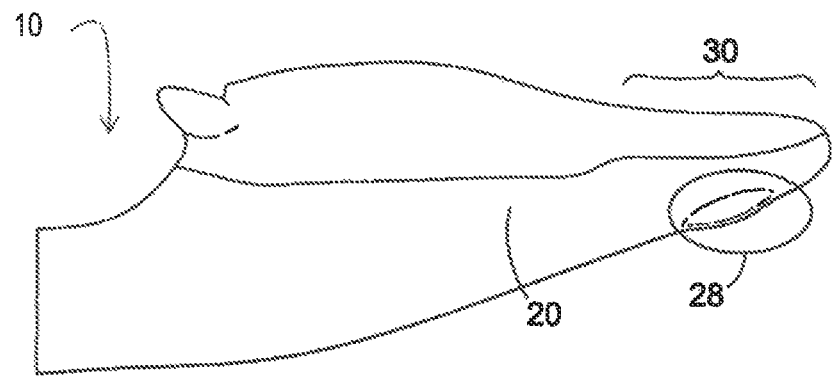
FIG. 4 illustrates a side view of the laryngeal cuff according to a first embodiment.
Figure 5:
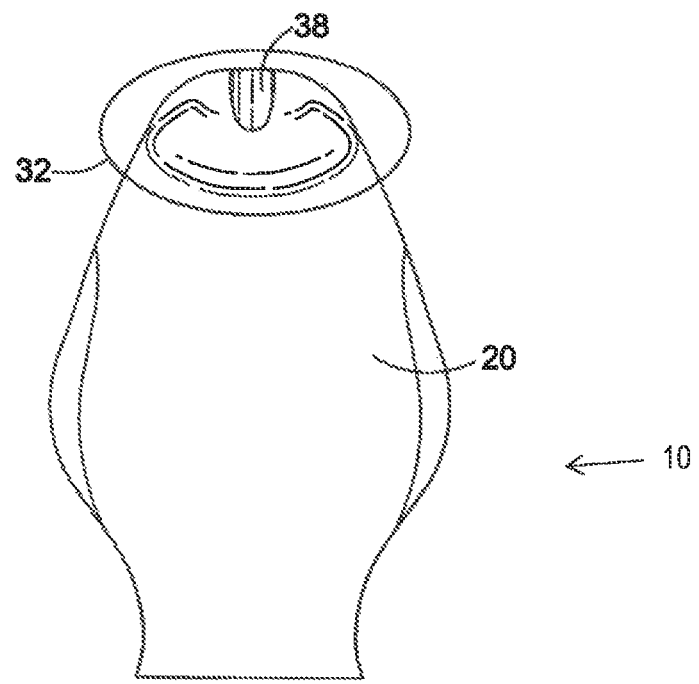
FIG. 5 illustrates a back dorsal view of the laryngeal cuff according to a first embodiment.
Figure 6:
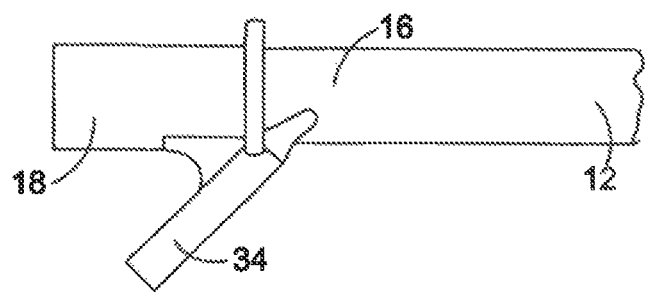
FIG. 6 illustrates a side view of the supplementary gas inlet according to a first embodiment.
Figure 7:
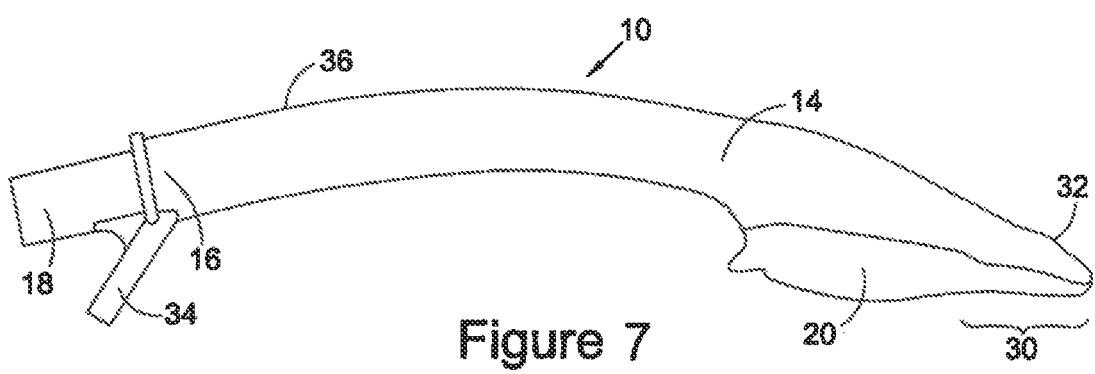
FIG. 7 illustrates a side view of the airway device according to a first embodiment.

Embodiments of the present invention are described below by way of example only. These examples represent the best ways of putting the invention into practice that are currently known to the applicant although they are not the only ways in which this could be achieved.

Referring to FIGS. 2 to 7, these illustrate an airway device 10 according to a first embodiment of the invention. The airway device 10 has an airway tube 12 having a first end 14 and a second end 16. The second end 16 optionally terminates in a 15 mm or other connector 18 suitable for connection to an anaesthetic breathing system of conventional type. Formed around the first end 14 of the airway tube is a laryngeal cuff 20. In the embodiment illustrated the laryngeal cuff 20 is non inflatable and is adapted in its shape and contours to correspond with the laryngeal inlet region of a patient.

The first end 14 of the airway tube 12 is also provided with an intubating ramp 22 configured to direct an endotracheal tube (or another other applicable tube or device) inserted through the airway tube 12 into the laryngeal inlet of the patient when the airway device 10 is in situ within a patient. The intubating ramp 22 ensures that the endotracheal tube, when inserted through the airway tube, follows its natural curve, rather than the curve of the airway tube 12, and guides the endotracheal tube into the laryngeal inlet of the patient when the airway device 10 is in situ in a patient.

In the embodiment illustrated the intubating ramp 2 is provided on the internal wall of the back dorsal side of the airway tube 12. In the alternative the intubating ramp 22 can instead be provided on the internal surface of the back dorsal side of the laryngeal cuff 20.

In addition to the provision of intubating ramp 22, the first end 14 of the airway tube 12 is of greater diameter and thus wider than the remainder of the airway tube 12. In the embodiment illustrated the internal surface of the front ventral side 24 of the airway tube 12 is flattened rather than curved to provide this widening. This further enables the endotracheal tube, when inserted through the airway tube 12, to follow its natural curve, rather than the curve of the airway tube 12 and works in combination with the intubating ramp 22.

In the embodiment illustrated the intubating ramp 22 is optionally provided with two channels 26, 28 that run longitudinally along the full length of the intubating ramp 22 from the first end to the second end thereof. The provision of the intubating ramp 22 reduces the depth of the internal cavity of the laryngeal cuff 20, this means that should the airway device 10 be sub-optimally inserted that there is risk that the airway of the patient could become partially occluded. The provision of the channels 26, 28 ensures the patency of the airflow through the airway device 10 into the airway of the patient without compromising the effect of the intubating ramp 22.

In the embodiment illustrated the tip 30 of the laryngeal cuff 20 is elongate compared to the prior art device illustrated in FIG. 1. In addition the tip 30 of the laryngeal cuff 20 is provided with a protrusion or bump 32 on the back dorsal side thereof. The elongate nature of the tip 30 of the laryngeal cuff 20 along with the dorsal protrusion or bump 32 both assist to provide an improved oesophageal seal when the airway device 10 is in situ in the patient. By providing an improved oesophageal seal there is reduced risk of inflation of the stomach of the patient, and a reduced risk of regurgitation entering into the airway of the patient.

In addition in the embodiment illustrated a side wall of the second end 16 of the airway tube 12 has been provided with an optional supplementary gas inlet 34, more particularly the supplementary gas inlet 34 is formed as part of connector 18, however in the alternative it may be separate from connector 18. The supplementary gas inlet 34 allows for additional oxygen or other gas to be provided to the patient if required.

In one alternative the laryngeal cuff is non-inflatable and is formed from any suitable soft plastics material. By way of a preferred softness (hardness) range, on the Shore A scale of Hardness, a hardness of less than 40 for the face of the laryngeal cuff that contacts the laryngeal inlet is optimum. By way of a preferred range, a value on the same scale of 000 to 20 is preferred, with a particularly preferred range of 000 to 4. The softness of the laryngeal cuff can be further adapted by forming cavities or channels within the body of the cuff itself.

In a further alternative the laryngeal cuff may be pre-filled with a fluid such as air, or other non-toxic gas, or a non-toxic liquid. In this context the term fluid has a broad meaning and includes any suitable gas, liquid, vapour or combination thereof and will be determined and designed by an expert in this field of anatomy/anaesthesia in conjunction with the materials specialist. The laryngeal cuff will be constructed of such a material which will not allow nitrous oxide (anaesthetic gas) to diffuse through the material to any significant amount so that the extra luminal pressure is kept constant. It follows therefore that the laryngeal cuff should be substantially impermeable to the fluid with which is filled and to anaesthetic gases.

Alternatively, the laryngeal cuff can be formed from a soft, foamed material or can be foam filled. In either case this provides a soft deformable but shaped surface around the face of the laryngeal cuff to engage over the anatomy of the larynx inlet region. Such a foam filled device will minimise any potential damage to the structures in that region whilst still providing a substantially complete seal.

Further in the alternative the laryngeal cuff is pre-filled during manufacture with a fluid in which case the lining of the cuff should be made from a material that does not absorb anaesthetic gases such as Nitrous Oxide, such that the pressure inside the cuff does not rise during use.

In another alternative the laryngeal cuff may be formed from a material which is adapted to absorb a liquid, such as water, mucous or blood or similar liquid material and in doing so to swell in size so as to confirm to the anatomical mucocartilagenous framework of the patient's laryngeal inlet. Such materials will be selected by the materials specialist but include CRM (cotton rayon mixes) as used in TAMPAX® tampons, or compressed Gel Foam 5.

In a further, alternative, the laryngeal cuff could take the form of a conventional, inflatable laryngeal cuff. The technology to form an inflatable laryngeal cuff is well known and need not be described here.

Finally, in yet another alternative, the laryngeal cuff may be hollow, but not inflatable in the traditional sense of the word, and instead Positive Pressure Ventilation is employed to "inflate" and self-pressurise the laryngeal cuff.

Also in the embodiment illustrated a buccal cavity stabiliser 36 has been provided around the airway tube 12 between the laryngeal cuff 20 and the second end 16 of the airway tube 12. The buccal cavity stabiliser 36 assists in locating and maintaining the position of the airway device 10 in use.

In the embodiment illustrated the buccal cavity stabiliser 36 is formed as an integral part of the airway tube 12, and further preferably the buccal cavity stabiliser 38, the airway tube 12 and the laryngeal cuff 20 are all formed as an integral unit.

In an alternative, no buccal cavity stabiliser 36 is provided.

A gastric tube passageway 38, separate to the airway tube 12 is provided which runs from an opening in the second end of the device near the connector 18 if provided to an opening in the tip of the cuff 20. The gastric tube passageway 38 allows for any gastric aspirate to be detected in the event of passive regurgitation during use. It also provides a route for the insertion of small-bore gastric tubes (e.g., Freka Tubes).

The device may be constructed from any suitable plastics material as selected by the materials specialist. Latex-free medical grade silicone rubber is one preferred material. The cuff should be soft in texture to avoid undue damage to the surrounding tissue. Other suitable materials for construction of this type of device include, but are not limited to, Poly Vinyl Chloride (PVC), Thermoplastic Elastomers such as the styrenic block copolymers (eg Styrene Butadiene Styrene (SBS), Styrene Ethylene Butylene Styrene (SEBS)), and Thermoplastic Olefin Blends (TPO), Thermoplastic PolyUrethanes (TPU), Copolyester (COPE), Polyether Block Amides (PEBAX) and foamed versions thereof, where appropriate.

A further important factor involved in the choice of a suitable material is transparency. Ideally the material or materials of construction should be substantially clear or transparent. This enables the anaesthetist or operator to see the inner lumen of the airway to check for blockages or other problems. Such transparent materials are known to the materials specialist.

The invention claimed is:

1. An airway device for human or animal use comprising an airway tube having a first end and a second end, wherein the first end of the airway tube is surrounded by a laryngeal cuff configured to fit over a laryngeal inlet of a patient when in situ, wherein the first end of the airway tube is provided with an intubating ramp disposed on an inner wall of the airway tube, the intubating ramp having a first end and a second end configured to direct a tube inserted through the airway tube into the laryngeal inlet of the patient when in situ, wherein the first end of the airway tube is of greater diameter than a remainder of the airway tube, and wherein an internal wall of the airway tube is curved other than a section of a ventral side of the airway tube, which section is flattened.

2. An airway device as claimed in claim 1 wherein the intubating ramp is provided on an internal wall of a dorsal side of the airway tube.

3. An airway device as claimed in claim 1 wherein the intubating ramp is provided with a channel.

4. An airway device as claimed in claim 3 wherein the channel runs longitudinally along the full length of the intubating ramp from the first end to the second end of the intubating ramp.

5. An airway device as claimed in claim 3 wherein the intubating ramp is provided with a plurality of channels.

6. An airway device as claimed in claim 1 wherein the laryngeal cuff has an elongate tip.

7. An airway device as claimed in claim 1 wherein a tip of the laryngeal cuff is provided with a protrusion on a back dorsal side thereof.

8. An airway device as claimed in claim 1 where a side wall of the second end of the airway tube is provided with a supplementary gas inlet.

* * * * *